United States Patent [19]

Moore, Jr. et al.

[11] Patent Number: 5,000,879
[45] Date of Patent: Mar. 19, 1991

[54] MELTING POINT ENHANCEMENT OF PARTIALLY BROMINATED DIPHENYL OXIDE MIXTURES

[75] Inventors: Robert M. Moore, Jr.; David R. Brackenridge, both of Baton Rouge, La.

[73] Assignee: Ethyl Corporation, Richmond, Va.

[21] Appl. No.: 387,776

[22] Filed: Aug. 1, 1989

[51] Int. Cl.$^5$ .................. C09K 21/08; C07C 43/29
[52] U.S. Cl. ................... 252/604; 252/601; 252/609; 568/639
[58] Field of Search ............... 568/639; 252/609, 601, 252/604

[56] References Cited

U.S. PATENT DOCUMENTS

| | | | |
|---|---|---|---|
| 3,518,316 | 6/1970 | Cumbo | 568/639 |
| 3,763,248 | 10/1973 | Mitchell | 260/649 |
| 3,833,674 | 9/1974 | Brackenridge | 568/639 |
| 4,214,103 | 7/1980 | Garman et al. | 568/639 |
| 4,740,629 | 4/1988 | Brackenridge | 568/639 |
| 4,835,322 | 5/1989 | Mamuzic et al. | 568/639 |

FOREIGN PATENT DOCUMENTS 1233643  10/1986  Japan .................. 568/639

*Primary Examiner*—Robert L. Stoll
*Assistant Examiner*—Joseph D. Anthony
*Attorney, Agent, or Firm*—E. E. Spielman, Jr.; David E. LaRose

[57] ABSTRACT

This invention relates to a process for increasing the melting point of partially brominated diphenyl oxide mixtures having an average bromine content of 7.2 to 7.7. The process comprises: forming a slurry comprised of $C_1$–$C_4$ alkanol and the mixture; maintaining the slurry until the melting point increase which is sought is obtained; and separating the so-treated mixture from the slurry.

11 Claims, No Drawings

MELTING POINT ENHANCEMENT OF PARTIALLY BROMINATED DIPHENYL OXIDE MIXTURES

BACKGROUND OF THE INVENTION

This invention relates to a process for increasing the melting point of mixtures of partially brominated diphenyl oxides having an average of 7.2 to 7.7 bromine atoms per molecule of diphenyl oxide.

The above mixtures are sold and denominated by the flame retardant industry as octabromodiphenyl oxide or as "Octabrom". For the sake of simplicity, these mixtures will hereinafter be referred to as Octabrom. Typically, the commercially significant Octabroms contain 0-2 weight percent pentabromodiphenyl oxide 5-15 weight percent hexabromodiphenyl oxide, 40-55 weight percent heptabromodiphenyl oxide, 30-40 weight percent octabromodiphenyl oxide, 5-15 weight percent nonabromodipnenyl oxide, and 0-2 weight percent decabromodiphenyl oxide. As can be appreciated, for any particular Octabrom, the average number of bromine atoms per molecule of brominated diphenyl oxide, hereinafter referred to as the bromine content, is dependent upon the amounts and the identities of the particular bromo homologs which are present in the mixture. The bromine content can be calculated by multiplying the weight percent of each bromo homolog by the number of bromine atoms in that homolog, adding the resulting products and dividing the sum by 100.

Octabrom has a melting point which is expressed as a temperature range since it does not exhibit a sharp melting point. Depending upon the process and any post-process treatment used for producing the Octabrom, the melting point can be low, e.g., mp 75° C.-95° C., high, e.g., mp 90° C.-145° C. or can be somewhere in-between.

It has been observed that the melting point of any particular Octabrom is an indicator of its amorphic or crystalline nature. The lower melting Octabroms are much less crystalline, i.e., more amorphic, than the higher melting Octabroms. Another difference between Octabroms with the lower melting points and Octabroms with the higher melting points is that the former has a tendency to form lumps and not to be free-flowing after being subjected to long storage periods, say a few weeks, and to elevated temperatures, e.g., 50° C. to 80° C., during the storage period.

Besides being an indication of the amorphic or crystalline nature of Octabrom and the tendency of the Octabrom to lump, the Octabrom melting point can also be a specification set by the Octabrom purchaser. Depending upon the use of the Octabrom, low melt or high melt Octabrom can be required.

THE INVENTION

This invention provides a process for treating Octabrom to increase its melting point. The process comprises: (i) forming a slurry of a $C_1$-$C_4$ alkanol and the Octabrom to be treated; (ii) maintaining the slurry for that period of time sufficient to obtain the increase in the Octabrom melting point which is sought; and (iii) recovering the treated Octabrom from the slurry.

For the purposes of this invention, it is to be understood that an increase in the Octabrom melting point is deemed to have been achieved when the treated Octabrom has a melting point in which the lowest temperature, the highest temperature or both the highest and lowest temperature, which define the Octabrom's melting point, are greater than the corresponding temperature(s) which define the melting point of the untreated Octabrom. It is also to be realized that there is a practical limit to the melting point increase which can be achieved by the process of this invention. It has been observed that after a maintenance period of about eight hours the increase in melting point slows. After a twenty-four hour maintenance period, the increase, while still occurring, is very slow. It is believed, though not confirmed, that after some period of time in excess of twenty-four hours the melting point increase will cease, with the obtainment of a maximum melting point of, say 120° C.-160° C.

The process of this invention is most useful in treating Octabrom having a relatively low melting point, for example, an Octabrom having a melting point in which the lowest temperature in the melting point rang is from about 65° C. to about 86° C. and in which the highest temperature in the rang is from about 95° C. to about 120° C. The value of such a treatment is that the low melting Octabrom is changed from one which can have a lumping problem, above discussed, to one in which the lumping problem is diminished or rendered nonexistent.

In addition to treating the relatively low melt Octabroms for the lumping problem, the process of this invention is of value in treating Octabrom having a higher melting point, say, one in which the lowest temperature in the melting point range is from about 87° C. to about 100° C. and in which the highest temperature in the range is from about 120° C. to about 135° C. While this Octabrom will generally not have a lumping problem, it still may be desirable to treat such an Octabrom so as to increase its melting point to meet a purchaser's higher melting point specifications. Octabroms having very high melting points, e.g., 100° C.-140° C., can also have their melting points raised by use of the long maintenance periods.

The $C_1$-$C_4$ alkanol used in forming the slurry is preferably methanol, ethanol or mixtures thereof. Methanol is most preferred. The term, $C_1$-$C_4$ alkanol, is meant to include individual alcohols containing from 1 to 4 carbon atoms and any mixtures of two or more of such alcohols. Exemplary individual alcohols are methanol, ethanol, propanol, isopropanol, butanol, isobutanol and t-butanol. Methanol and ethanol are preferred, with methanol being most preferred.

The slurry can be formed by adding the alkanol to the Octabrom or vice versa, there being no criticality accorded to the order of addition. The amount of alkanol used is that amount which is sufficient to form a readily agitatable slurry. Generally, a slurry containing from about 40 weight percent to about 90 weight percent alkanol is suitable, with a slurry containing from about 50 weight percent to about 75 weight percent alkanol being most preferred. The foregoing weight percentages are based upon the total weight of the slurry.

It is not deleterious to the process of this invention if the alkanol is accompanied by minor amounts of water, say less than 5 weight percent water. However, large amounts of water, e.g., 50 to 30 weight percent water, should be avoided since the enhancement of the Octabrom melting point by the process is diminished.

A slurry is formed since Octabrom is not very soluble in $C_1$-$C_4$ alkanols. Indeed, Octabrom has only about a 0.5 grams/100 grams of alkanol solubility at 23° C. Due to the low solubility of Octabrom in alkanol, there is little difference in the bromo homolog distribution between the untreated Octabrom and the treated Octabrom. Thus, product specifications are not adversely affected. Further, the low solubility results in there being insignificant Octabrom loss (<1 weight percent) from use of the process of this invention.

One unusual aspect of the instant process is that the alkanol can be reused many times without concern for a build-up of solubles therein. It has been found that after the first use, the solubles in the alkanol amount from about 0.2 to about 0.7 weight percent, based upon the total weight of the solution. Thereafter, no significant increase in the solubles content is seen even when the alkanol is used five or more times. Even further, the bromo homolog content, as solubles in the alkanol, exhibits a fairly even distribution irrespective of the number of times the alkanol is used.

The slurry is maintained for that period of time needed to obtain the increase in the Octabrom melting point which is sought. The time period needed for each situation is determined empirically. Generally, maintenance periods from about 1 to about 6 hours are sufficient for most situations. A preferred maintenance period is from about 2 to about 4 hours. The longest maintenance periods will be needed when effecting the largest increases in the Octabrom melting point.

The maintenance period can be shortened by grinding the Octabrom to be treated to reduce its particle size and/or by agitating the slurry for at least a portion of the maintenance period. Agitation of the slurry can be accomplished by any conventional means, such as by stirring. The maintenance period preferably occurs at ambient temperature, there being no observed advantage from using higher than ambient temperatures. Temperatures within the range of from about 20° C. to about 45° C. are suitable. Temperatures approaching the alkanol reflux temperature should be avoided as a gum-like substance can be formed. The pressure during the maintenance period is conveniently atmospheric. Super-atmospheric pressure can be used to prevent alkanol loss during the maintenance period.

After the maintenance period is complete, the treated Octabrom can be recovered from the slurry by any solid-liquid separation technique which does not harm the treated Octabrom. Simple filtration, centrifugation, etc. are suitable techniques.

The recovered treated Octabrom will initially contain entrained alkanol. To remove the alkanol, the treated Octabrom can be washed with water several times. After the water washing, the treated Octabrom is dried conventionally.

The following examples illustrate some of the features of this invention and are not to be taken as limiting the scope of the invention.

EXAMPLES I-V

For each example, 25 g methanol and 25 g of finely ground Saytex ® 111 flame retardant were added to a 300 mL flask fitted with a mechanical stirrer. Saytex ® 111 flame retardant is an Octabrom product having a melting point of 80° C.-100° C., ±2° C. The mechanical stirrer was activated to agitate the slurry. The maintenance time for each example is shown in Table I. The agitation was conducted over the entire maintenance period. After the maintenance period, the treated Saytex ® 111 flame retardant was separated from the methanol by filtration and allowed to air dry for about one hour. After air drying, the Octabrom was heated to 50° C. for one hour (Examples I-IV) and to 70° C. for one hour (Example V). The so-heated Octabrom was then visually inspected for lumping.

The melting point of the untreated Saytex ® 111 flame retardant and the melting points shown in Table I were obtained with a Thomas Hoover melting point apparatus sold by Arthur H. Thomas Co. of Philadelphia, Pa.

TABLE I

| Example No. | Maintenance Time | Melting Point - Treated Saytex ® III Flame Retardant | Lumping Characteristics |
|---|---|---|---|
| Untreated Octabrom | 0 min. | 80° C.-100° C. | Lumping |
| I | 45 min. | 86° C.-120° C. | Some Lumping |
| II | 2.25 hr. | 89° C.-145° C. | No Lumping |
| III | 3.0 hr. | 90° C.-145° C. | No Lumping |
| IV | 4.5 hr. | 92° C.-140° C. | No Lumping |
| V | 6.5 hr. | 97° C.-140° C. | No Lumping |

EXAMPLE VI

To a 300 mL flask was added 25 g of ethanol and 25 g of Saytex ® 111 flame retardant. Before the addition, the Saytex ® 111 flame retardant had a melting point of 76° C.-98° C., ±2° C. A slurry was observed. After 24 hours of sitting in the flask, no stirring, the treated Octabrom product was recovered by filtration and allowed to air dry for about 1-2 hours. The melting point of the dry treated Octabrom, as determined with a Thomas Hoover melting point apparatus, was 107° C.-127° C.

EXAMPLE VII

The procedure of Example VI was repeated except that isopropanol was used instead of ethanol. The dried treated Octabrom had a melting point of 85° C.-105° C.

EXAMPLE VIII

A four-cycle experiment was run using the apparatus of Example I. For the first cycle, 25 g of methanol and 25 g of Saytex ® 111 flame retardant was added to the flask. The maintenance period was for four hours with the mechanical stirrer being activated during that period. The heated Saytex ® 111 flame retardant was recovered by filtration.

For cycles 2, 3 and 4, the same procedure as above was used except that the 25 g of methanol added to the flask was provided by the methanol filtrate from the previous cycle and by make-up methanol to bring the total to 25 g. Samples of the recovered treated Saytex ® 111 flame retardant and of the methanol filtrate from each of the cycles was analyzed by Gas Chromatography. The analysis for the Saytex ® 111 flame retardant was carried out by dissolving each of the samples of the treated Saytex ® 111 flame retardant in toluene to form a one percent solution and injecting the solution into a DB-1 column. Tables II and III give the results.

TABLE II

| Octabrom Isomer Distribution in Methanol Filtrate as Area % | | | | |
|---|---|---|---|---|
| Isomer | Cycle 1 | Cycle 2* | Cycle 3* | Cycle 4* |
| $Br_6$ | 18.06 | 23.02 | 23.08 | 21.3 |
| $BR_7$ | 52.13 | 58.27 | 55.89 | 57.99 |
| $BR_8$ | 24.28 | 17.46 | 18.60 | 18.17 |
| $BR_9$ | 5.19 | 2.17 | 2.41 | 2.09 |

TABLE II-continued

| Octabrom Isomer Distribution in Methanol Filtrate as Area % | | | | |
|---|---|---|---|---|
| Isomer | Cycle 1 | Cycle 2* | Cycle 3* | Cycle 4* |
| $BR_{10}$ | 0.34 | 0 | 0 | 0 |

*Each area % value is an average of two measurements

TABLE III

| Isomer Distribution of Treated Saytex 111 Flame Retardant as Area % | | | | |
|---|---|---|---|---|
| Isomer | Cycle 1* | Cycle 2* | Cycle 3* | Cycle 4* |
| $BR_6$ | 10.72 | 10.57 | 8.65 | 9.33 |
| $BR_7$ | 48.11 | 47.09 | 45.13 | 46.83 |
| $BR_8$ | 34.53 | 34.74 | 37.63 | 36.34 |
| $BR_9$ | 6.48 | 7.14 | 8.13 | 7.24 |
| $BR_{10}$ | 0.165 | 0.45 | 0.46 | 0.26 |

*Each area % value is an average of two measurements

Octabrom is a commercially available flame retardant which is well known to the art. Octabrom is conventionally produced by reacting bromine in an amount which is 80 to 100 percent in excess of the stoichiometric amount with diphenyl oxide in the presence of iron catalyst.

What is claimed:

1. A process for treating a mixture of partially brominated diphenyl oxides in solid form having a average of from about 7.2 to about 7.7 bromine atoms per molecule of diphenyl oxide so as to increase the melting point of the mixture, said process comprising:
   (a) forming a slurry comprised of $C_1$–$C_4$ alkanol and the mixture to be treated;
   (b) maintaining the slurry for a period of time sufficient to obtain the increase in the mixture's melting point which is sought; and
   (c) recovering the treated mixture from the slurry.

2. The process of claim 1 wherein the partially brominated diphenyl oxide contains hexabromodiphenyl oxide, heptabromodiphenyl oxide, octabromodiphenyl oxide, nonabromodiphenyl oxide and, optionally, either pentabromodiphenyl oxide, decabromodiphenyl oxide or both pentabromodiphenyl oxide and decabromodiphenyl oxide.

3. The process of claim 1 wherein the $C_1$–$C_4$ alkanol is either methanol, ethanol or a mixture thereof.

4. The process of claim 1 wherein the $C_1$–$C_4$ alkanol comprises from about 40 weight percent to about 90 weight percent of the slurry.

5. The process of claim 1 wherein the $C_1$–$C_4$ alkanol comprises from about 50 weight percent to about 75 weight percent of the slurry.

6. The process of claim 1 wherein the maintenance period is from about 1 to about 6 hours.

7. The process of claim 1 wherein the maintenance period is from about 2 to about 4 hours.

8. The process of claim 1 wherein the maintenance period is less than 24 hours.

9. The process of claim 1 wherein the slurry is agitated during at least a portion of the maintenance period.

10. The process of claim 1 wherein the slurry is maintained at a temperature within the range of from about 20° C. to about 45° C.

11. The process of claim 1 wherein the partially brominated diphenyl oxide contains hexabromodiphenyl oxide, heptabromodiphenyl oxide, octabromodiphenyl oxide, nonabromodiphenyl oxide and optionally either pentabromodiphenyl oxide, decabromodiphenyl oxide or both pentabromodiphenyl oxide and decabromodiphenyl oxide; the $C_1$–$C_4$ is either methanol, ethanol, or a mixture thereof; the $C_1$–$C_4$ comprises from about 40 weight percent to 90 weight percent of the slurry; the maintenance period is less than 24 hours; and the slurry is agitated during at least a portion of the maintenance period.

* * * * *

UNITED STATES PATENT AND TRADEMARK OFFICE
CERTIFICATE OF CORRECTION

PATENT NO. : 5,000,879

DATED : March 19, 1991

INVENTOR(S) : Robert M. Moore, Jr. and David R. Brackenridge

It is certified that error appears in the above-identified patent and that said Letters Patent is hereby corrected as shown below:

Column 6, line 10, reads "claim I" and should read --claim 1--.

Signed and Sealed this

Fifth Day of January, 1993

*Attest:*

DOUGLAS B. COMER

*Attesting Officer*     *Acting Commissioner of Patents and Trademarks*